United States Patent
Safronov et al.

(10) Patent No.: US 10,179,795 B2
(45) Date of Patent: Jan. 15, 2019

(54) SYNTHESIS OF AMINE BORANES AND POLYHEDRAL BORANES

(71) Applicants: Alexander Valentinovich Safronov, Columbia, MO (US); Satish Subray Jalisatgi, Columbia, MO (US); Marion Frederick Hawthorne, Columbia, MO (US)

(72) Inventors: Alexander Valentinovich Safronov, Columbia, MO (US); Satish Subray Jalisatgi, Columbia, MO (US); Marion Frederick Hawthorne, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/116,375

(22) PCT Filed: Feb. 3, 2015

(86) PCT No.: PCT/US2015/014234
§ 371 (c)(1),
(2) Date: Aug. 3, 2016

(87) PCT Pub. No.: WO2015/117123
PCT Pub. Date: Aug. 6, 2015

(65) Prior Publication Data
US 2017/0066785 A1 Mar. 9, 2017

Related U.S. Application Data

(60) Provisional application No. 61/965,675, filed on Feb. 3, 2014.

(51) Int. Cl.
*C07F 5/02* (2006.01)
*C07F 5/05* (2006.01)

(52) U.S. Cl.
CPC ............... *C07F 5/022* (2013.01); *C07F 5/05* (2013.01)

(58) Field of Classification Search
None
See application file for complete search history.

(56) References Cited

U.S. PATENT DOCUMENTS

| 3,108,139 A | 10/1963 | Larchar, Sr. et al. |
| 3,227,754 A | 1/1966 | Bragdon et al. |
| 3,373,202 A | 3/1968 | Makhlouf et al. |
| 3,373,203 A | 3/1968 | Makhlouf et al. |
| 5,582,808 A | 12/1996 | Patek |
| 6,086,837 A | 7/2000 | Cowan et al. |
| 7,524,477 B2 | 4/2009 | Spielvogel et al. |
| 7,641,897 B2 | 1/2010 | Weissman et al. |
| 7,718,154 B2 | 5/2010 | Ivanov et al. |
| 2004/0249215 A1 | 12/2004 | Suda et al. |
| 2005/0080048 A1 | 4/2005 | Tavassoli et al. |
| 2005/0169827 A1 | 8/2005 | Spielvogel et al. |
| 2005/0169828 A1 | 8/2005 | Spielvogel et al. |
| 2006/0286019 A1 | 12/2006 | Ivanov et al. |
| 2006/0286020 A1 | 12/2006 | Ivanov et al. |

FOREIGN PATENT DOCUMENTS

| FR | 2 584 398 | 1/1987 |
| WO | WO 2013/115889 | 8/2013 |

OTHER PUBLICATIONS

Supplementary European Search Report dated Sep. 7, 2017 for corresponding EP 3102586 filed on Feb. 3, 2015 (8 pgs).
Database WPI, Abstract, Week 201434, Thomson Scientific, London, GB; AN 2014-K04555 & CN 103694267A; XP002772985, Apr. 2, 2014. (2 pgs).
Mongeot, H. et al., Article, "(Et4N)2B10H10 et (Et4N)2B12H12: synthese de Et4NBH4, separation et purification", Bulletin de la Societe Chimique de France, Societe Francaise de Chimie, Paris, France, vol. 3 (Jan. 1, 1986), pp. 385-389. (6 pgs) (Text of Article is in French).
Atkinson et al., *Syntheses of the alkali metal borodeuterids*, Canadian J. of Chem. vol. 45, 1967.
Colombier, et al., *Studies of the Pyrolysis of Tetraethylammonium Tetrahydroborate*, Inorganica Chimica Acta, 115 (1986) 11-16.
Adams et al., *A New Synthetic Route to Boron-10 Enriched Pentaborane(9) from Boric Acid and Its Conversion to anti-$^{10}B_{18}H_{22}$*, J.Am. Chem. Soc., vol. 124, No. 25, pp. 7292-93, 2002.
Sivaev, et al., *Chemistry of closo-Dodecaborate Anion $[B_{12}H_{12}]^{2-}$: A Review*, Collection of Czechoslovak Chemical Comm 67(6) (2002) 679-727.
International Search Report and Written Opinion dated May 7, 2015 issued for priority PCT/US2015/14234 filed on Feb. 3, 2015 (8 pgs).
International Search Report and Written Opinion dated Apr. 23, 2015 issued for priority PCT/US2015/14224 filed on Feb. 3, 2015 (11 pgs).

*Primary Examiner* — Ana Z Muresan
(74) *Attorney, Agent, or Firm* — Stinson Leonard Street LLP

(57) ABSTRACT

The present invention relates in general to a method for the synthesis and purification of 1) the polyhedral borane decahydrodecaborate and dodecahydrododecaborate anions and their salts and 2) amines and amine boranes. The organoammonium halide is combined with alkali metal tetrahydroborate to form organoammonium tetrahydroborate, which upon pyrolysis provides organoammonium decahydrodecaborate and organoammonium dodecahydrododecaborate.

34 Claims, No Drawings

SYNTHESIS OF AMINE BORANES AND POLYHEDRAL BORANES

CROSS-REFERENCE TO RELATED APPLICATIONS

This application is based on and claims priority to U.S. Provisional Application Ser. No. 61/965,675 filed on Feb. 3, 2014, which is hereby incorporated herein by reference.

STATEMENT REGARDING FEDERALLY SPONSORED RESEARCH OR DEVELOPMENT

This invention was made with government support under Grant No. W15QKN-06-D-0031 awarded by the U.S. Army. The government has certain rights in the invention.

BACKGROUND OF THE INVENTION

1. Field of the Invention

The present invention relates in general to methods for the synthesis and purification polyhedral boranes, their salts, amines and amine boranes.

2. Description of Related Art

Existing methods of producing salts of polyhedral borane anions from borohydrides are typically based on pyrolysis of tetraalkylammonium borohydrides in the presence of a high-boiling alkane solvent. The reliability of many of the developed methods is questionable, especially of those methods that claim selective formation of the decahydrodecaborate anion.

Isotopically enriched boron-10 compounds, such as salts of polyhedral boranes closo-decahydrodecaborate and closo-dodecahydrododecaborate, can be used in research laboratories for the preparation of therapeutic agents for the boron neutron capture therapy of cancer (BNCT). However, these compounds are not commercially accessible. As a result, there is a need to provide a straightforward and easily scalable method for the synthesis, isolation, and purification of boron-10 isotopically-enriched compounds.

BRIEF SUMMARY OF THE INVENTION

In one aspect, the present invention is directed to a process for the synthesis of mixtures of salts of polyhedral boranes and includes the steps of first, combining a methyltriethylammonium halide with an alkali metal tetrahydroborate in a reaction mixture; second, reacting the methyltriethylammonium halide and the alkali metal tetrahydroborate to form a methyltriethylammonium tetrahydroborate intermediate and an alkali metal halide; and third, pyrolizing the methyltriethylammonium tetrahydroborate intermediate to produce a product mixture comprising methyltriethylammonium decahydrodecaborate and methyltriethylammonium dodecahydrododecaborate. Preferably, the methyltriethylammonium halide is either methyltriethylammonium chloride or methyltriethylammonium bromide. The alkali metal tetrahydroborate is preferably either sodium tetrahydroborate or potassium tetrahyrdroborate.

In one embodiment of the first aspect of the invention, the reacting step and the pyrolizing step are performed as a continuous heating step, and the pyrolizing step comprises pyrolizing the methyltriethylammonium tetrahydroborate intermediate in situ in the reaction mixture.

In one embodiment of the first aspect of the invention, prior to the reacting step of first aspect of the process of the invention, a polar aprotic solvent is added to the reaction mixture; and prior to the pyrolizing step, the methyltriethylammonium tetrahydroborate intermediate is separated from the reaction mixture. Preferably, the polar aprotic solvent is dimethylformamide, dimethylacetamide, dimethylsulfoxide, sulfolane, or hexamethylphosphoramide. In such an embodiment, the intermediate separating step comprises filtering the reaction mixture to produce a filtrate comprising the methyltriethylammonium tetrahydroborate intermediate and precipitating the methyltriethylammonium tetrahydroborate intermediate from the filtrate with a second solvent. Preferably, the second solvent is a linear or cyclic ether such as diethyl ether, tetrahydrofuran, 1,4-dioxane, and dimethoxyethane.

In one embodiment of the first aspect of the invention, the methyltriethylammonium decahydrodecaborate and the methyltriethylammonium dodecahydrododecaborate in the product mixture may be separated based on water solubility.

In such an embodiment where the product mixture contains the alkali metal halide, the product mixture separating step preferably includes first combining the product mixture with cold water to produce a product mixture solution; and second, filtering the product mixture solution to produce a filter cake comprising methyltriethylammonium dodecahydrododecaborate and a product mixture filtrate comprising methyltriethylammonium decahydrodecaborate, methyltriethylammonium dodecahydrododecaborate and the alkali metal halide. Preferably, the methyltriethylammonium dodecahydrododecaborate is purified from the filter cake. A preferred purifying step includes dissolving the filter cake in acetonitrile and recrystallizing the methyltriethylammonium dodecahydrododecaborate from the acetonitrile to produce a crystalline residue comprising the methyltriethylammonium dodecahydrododecaborate. The methyltriethylammonium decahydrodecaborate is preferably removed from the product mixture filtrate. One preferred method of removal includes first evaporating the water in the product mixture filtrate to form a residue comprising the methyltriethylammonium decahydrodecaborate; second, re-dissolving the residue in additional water to produce a methyltriethylammonium decahydrodecaborate solution; third, filtering the methyltriethylammonium decahydrodecaborate solution to form a second filtrate comprising the methyltriethylammonium decahydrodecaborate; and fourth, precipitating the decahydrodecaborate dianion from the second filtrate. The precipitating step preferably includes adding to the second filtrate a halide such as trialkylammonium halides, tetraalkylammonium halides and ammonium halide. Acceptable ammonium halides include but are not limited to tetrabutylammonium bromide, tetrabutylammonium chloride, tributylammonium chloride, and tributylammonium bromide. In an alternative embodiment, the decahydrodecaborate dianion can be isolated from the second filtrate using an ion exchange resin.

In embodiments where the product mixture is substantially free of the alkali metal halide, the product mixture separating step preferably includes first combining the product mixture with cold water to produce a product mixture solution and second filtering the product mixture solution to produce a filter cake comprising methyltriethylammonium dodecahydrododecaborate and a product mixture filtrate comprising methyltriethylammonium decahydrodecaborate. Preferably, the methyltriethylammonium dodecahydrododecaborate is purified from the filter cake. The purifying step preferably includes dissolving the filter cake in acetonitrile and recrystallizing the methyltriethylammonium dodecahydrododecaborate from the acetonitrile to produce a crystalline residue comprising the methyltriethylammonium dodecahydrododecaborate. The product mixture separating step preferably includes precipitating the decahydrodecaborate dianion from the product mixture filtrate. Preferably, the decahydrodecaborate dianion is precipitated by adding to the product mixture filtrate a halide such as trialkylammonium halides, tetraalkylammonium halides and ammonium halides. Acceptable ammonium halides include but are not limited to tetrabutylammonium bromide, tetrabutylammonium chloride, tributylammonium chloride, and tributylammonium bromide. In an alternative embodiment, the decahydrodecaborate dianion can be isolated from the second filtrate using an ion exchange resin.

In one embodiment of the first aspect of the invention, the pyrolizing step is conducted in a reactor attached to a two-stage condensation system, wherein a first stage condenser collects a mixture of methyldiethylamine borane, triethylamine borane, methyldiethylamine, and triethylamine, and a second stage condenser collects a mixture of methyldiethylamine and triethylamine. The mixture of methyldiethylamine borane, triethylamine borane, methyldiethylamine, and triethylamine may be collected and distilled by fractional distillation to separate the methyldiethylamine borane, triethylamine borane, methyldiethylamine, and triethylamine. The mixture of methyldiethylamine and triethylamine may be collected and distilled by fractional distillation to separate the methyldiethylamine and triethylamine.

In one embodiment, the alkali metal tetrahydroborate is $^{10}$B-enriched alkali metal tetrahydroborate. The $^{10}$B-enriched alkali metal tetrahydroborate may be synthesized by first, reacting $^{10}$B-enriched boric acid with a $C_2$-$C_4$ alcohol in a reaction mixture that does not include toluene, xylene, mesitylene, benzene, or 1,2-dichlorhoethane to produce trialkylborate-$^{10}$B; second, reacting the trialkylborate-$^{10}$B with a metal aluminum hydride in the presence of amine to produce amine borane-$^{10}$B; and third, reacting the amine borane-$^{10}$B with a reagent selected from the group consisting of alkali metal hydride and alkali metal methoxide to produce alkali metal tetrahydroborate-$^{10}$B.

In one embodiment of the first aspect of the invention, the pyrolizing step is conducted at a temperature between 180° C. and 200° C. for between 1 and 4 hours.

In certain embodiments, the present invention is directed to a method for synthesizing mixtures of salts of polyhedral boranes that includes first combining a methyltriethylammonium halide with an alkali metal tetrahydroborate in a reaction mixture; and second, pyrolizing the reaction mixture to produce a product mixture comprising methyltriethylammonium decahydrodecaborate, methyltriethylammonium dodecahydrododecaborate and an alkali metal.

In certain embodiments, the present invention is directed to a method for synthesizing mixtures of salts of polyhedral boranes that includes first combining a methyltriethylammonium halide, an alkali metal tetrahydroborate and a solvent selected from the group consisting of dimethylformamide, dimethylacetamide, dimethylsulfoxide, and sulfolane, hexamethylphosphoramide to form a methyltriethylammonium tetrahydroborate intermediate and an alkali metal halide; second, separating the methyltriethylammonium tetrahydroborate intermediate from the reaction mixture; and third, pyrolizing the methyltriethylammonium tetrahydroborate intermediate to produce a product mixture comprising methyltriethylammonium decahydrodecaborate and methyltriethylammonium dodecahydrododecaborate, wherein the product mixture is substantially free of the alkali metal halide.

In certain embodiments, the present invention is directed to a method for separating a methyltriethylammonium decahydrodecaborate and a methyltriethylammonium dodecahydrododecaborate from a mixture based on water solubility wherein the separating step includes first combining the mixture with cold water to produce a mixture solution; and second, filtering the mixture solution to produce a filter cake comprising methyltriethylammonium dodecahydrododecaborate and a product mixture filtrate comprising methyltriethylammonium decahydrodecaborate.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a process for the synthesis and purification of the polyhedral borane anions, decahydrodecaborate and dodecahydrododecaborate, and their salts. In the reaction, a methyltriethylammonium halide is combined with an alkali metal tetrahydroborate in a reaction mixture. The methyltriethylammonium halide and the alkali metal tetrahydroborate are reacted to form a methyltriethylammonium tetrahydroborate intermediate and an alkali metal halide. The methyltriethylammonium tetrahydroborate intermediate is pyrolized to produce a product mixture of methyltriethylammonium decahydrodecaborate and methyltriethylammonium dodecahydrododecaborate. The alkali metal tetrahydroborate may be $^{10}$B-enriched, and the resulting products may comprise $^{10}$B-enriched decahydrodecaborate and decahydrodecaborate dianions and salts.

In one exemplary embodiment, the reacting step and the pyrolizing step are performed in a continuous heating step. In such an embodiment, the methyltriethylammonium tetrahydroborate intermediate is pyrolized in situ in the reaction mixture. The resulting product mixture of methyltriethylammonium decahydrodecaborate and methyltriethylammonium dodecahydrododecaborate also contains the alkali metal halide.

In a second exemplary embodiment, the methyltriethylammonium tetrahydroborate intermediate is separated from the reaction mixture prior to pyrolysis. In one such embodiment, a solvent is added to the reaction mixture, prior to pyrolysis, and the resulting reaction produces the methyltriethylammonium tetrahydroborate intermediate. The methyltriethylammonium tetrahydroborate intermediate is separated from the reaction mixture and is then pyrolized to produce a product mixture of methyltriethylammonium decahydrodecaborate and methyltriethylammonium decahydrodecaborate. The product mixture is substantially free of the alkali metal halide.

In both embodiments, the methyltriethylammonium decahydrodecaborate and the methyltriethylammonium dodecahydrododecaborate in the product mixture may be separated based on water solubility. The decahydrodecaborate and dodecahydrododecaborate dianions are recovered as salts.

The present invention is also directed to the synthesis of amines and amine boranes, which are produced as by-products of the pyrolysis and can be separated by condensation and purified through distillation.

First Exemplary Embodiment—Synthesis and Purification of Polyhedral Borane Salts Synthesis of Polyhedral Borane Salts In a first exemplary embodiment, the methyltriethylammonium halide, such as methyltriethylammonium chloride or methyltriethylammonium bromide, is dried in a reaction vessel. The alkali metal tetrahydroborate, such as sodium tetrahydroborate or potassium tetrahydroborate, is subsequently added to the reaction vessel. The molar ratio of alkali metal tetrahydroborate to methyltriethylammonium halide is preferably 0.9:1.0 to 1.1:1.0, and in certain embodiments is about 1:1.

The reaction mixture is stirred in a reaction vessel and heated. The reaction may be conducted in a horizontal or vertical type reactor. The reaction vessel is preferably connected to a distillation device so that gases may safely escape the reactor and be condensed, as discussed in more detail below with respect to "Isolation of Amines and Amine Boranes" below.

The heating step, which can also be referred to as a pyrolysis step, comprises heating the reaction mixture in a continuous heating step to (i) allow the reaction between the solid methyltriethylammonium halide and alkali metal tetrahydroborate to occur and form the methyltriethylammonium tetrahydroborate intermediate, and (ii) allow pyrolysis of the methyltriethylammonium tetrahydroborate intermediate. In certain embodiments, the reaction and pyrolysis occur concurrently for at least a portion of the reaction. The temperature may be raised gradually to the pyrolysis temperature over one hour or more, and may be held at an intermediate temperature between 120° C. to 150° C. for a period of time, such as one hour. Alternatively, the temperature may be quickly raised to the pyrolysis temperature over a period of one hour or less. The pyrolysis temperature is preferably at least 180° C. and in certain embodiments is between 180 and 200° C. The reaction mixture is held at the pyrolysis temperature for a period of time sufficient to allow the pyrolysis to take place. In certain embodiments, the reaction mixture is held at the pyrolysis temperature for at least one hour, or between one and four hours. The reaction mixture is subsequently allowed to cool to room temperature.

The resulting product mixture contains a mixture of methyltriethylammonium decahydrodecaborate and methyltriethylammonium dodecahydrododecaborate, as well as the unreacted alkali metal halide. In certain embodiments, the ratio, by weight, of methyltriethylammonium decahydrodecaborate to methyltriethylammonium dodecahydrododecaborate in the product mixture can range between 40:60 and 60:40.

Isolation of Polyhedral Borane Salts

The methyltriethylammonium decahydrodecaborate and methyltriethylammonium dodecahydrododecaborate in the product mixture, which also contains the alkali metal halide, are subsequently separated based on water solubility.

The product mixture is mixed with cold water. The temperature of the cold water is below 5° C., preferably between 0° C. and 10° C. and in certain embodiments the cold water is ice water at a temperature of about 0° C. The water may be in the form of an aqueous solution, such as a sodium chloride solution. The resulting product mixture solution comprises sufficient water to dissolve the product mixture. The product mixture may comprise between about 25% and 35% (w/w) of the product mixture solution, and in certain embodiments comprises about 30% (w/w) of the product mixture solution. The resulting product mixture solution is stirred to dissolve the product mixture in the product mixture solution, preferably for at least 2 minutes.

The product mixture solution is filtered to produce a filter cake comprising the methyltriethylammonium dodecahydrododecaborate and a product mixture filtrate comprising methyltriethylammonium decahydrodecaborate, small amounts of methyltriethylammonium dodecahydrododecaborate and the alkali metal halide. The product mixture filtration step may be repeated one or more times. The methyltriethylammonium decahydrodecaborate and methyltriethylammonium dodecahydrododecaborate are further separated as follows:

Separation of Dodecahydrododecaborate

The filter cake is recrystallized from acetonitrile to produce a crystalline residue comprising the methyltriethylammonium dodecahydrododecaborate. In such recrystallization, the filter cake is dissolved in acetonitrile and the methyltriethylammonium dodecahydrododecaborate is recrystallized from the acetonitrile to produce the crystalline residue comprising the methyltriethylammonium dodecahydrododecaborate. The resulting crystalline residue is then washed and dried, in certain embodiments with acetone, to yield the methyltriethylammonium dodecahydrododecaborate polyhedral borane salt comprising the dodecahydrododecaborate dianion. The anion may be a closo-dodecahydrododecaborate anion. The recovery of the closo-dodecahydrododecaborate salt can achieve at least 50% recovery of the dodecahydrododecaborate dianion, and in some embodiments 65-75% recovery can be achieved.

Separation of Decahydrodecaborate

The water in the product mixture filtrate is evaporated until the resulting residue comprising the methyltriethylammonium decahydrodecaborate is dry. The dry residue is then re-dissolved in hot water to form a methyltriethylammonium decahydrodecaborate solution. The water is at least 90° C. and in certain embodiments is boiling water. The solution is subsequently filtered to remove residual methyltriethylammonium dodecahydrododecaborate from the solution, and the methyltriethylammonium decahydrodecaborate is collected in a second filtrate.

After cooling, the decahydrodecaborate dianion is precipitated from the second filtrate as a salt. The decahydrodecaborate dianion may be precipitated from the second filtrate using an ammonium halide. Other compounds that can be used to precipitate the decahydrodecaborate dianion include tetraalkylphosphonium halides. The ammonium halide may be selected from the group consisting of trialkylammonium halides and tetraalkylammonium halides. In certain embodiments, the ammonium halide is selected from the group consisting of tetrabutylammonium bromide, tetrabutylammonium chloride, tributylammonium chloride, and tributylammonium bromide to produce the corresponding ammonium decahydrodecaborate salts. The halide is added to the second filtrate in an amount sufficient to precipitate the decahydrodecaborate dianion as an ammonium decahydrodecaborate salt. In certain embodiments the halide is added in an amount that is at least twice the number of moles of the decahydrodecaborate dianion and in certain embodiments, the molar ratio of halide to decahydrodecaborate dianion is 2.5:1. The decahydrodecaborate salt precipitate is washed with water. The salt may be a closo-decahydrodecaborate salt. The percentage recovery of the decahydrodecaborate anion ($[B_{10}H_{10}]^{2-}$) can reach at least 50% and in certain embodiments can reach 75-80%.

In certain embodiments, the decahydrodecaborate anion is not precipitated as an ammonium salt, but is isolated and collected from the second filtrate using an ion exchange resin. In one such embodiment, the methyltriethylammonium cation is exchanged for alkali metal cations or ammonium by adding alkali metal or ammonium hydroxide to the ion exchange resin. The decahydrodecaborate is recovered as an alkali metal or ammonium salt of the decahydrodecaborate dianion.

Second Exemplary Embodiment—Synthesis and Purification of Polyhedral Borane Salts Synthesis of Polyhedral Borane Salts In a second exemplary embodiment, the methyltriethylammonium halide, such as methyltriethylammonium chloride or methyltriethylammonium bromide, and alkali metal tetrahydroborate, such as sodium tetrahydroborate or potassium tetrahydroborate, are mixed as solids. The methyltriethylammonium halide may be anhydrous. The molar ratio of alkali metal tetrahydroborate to methyltriethylammonium halide is preferably 0.9:1 to 1.1:1, and in certain embodiments is about 1:1.

A solvent is added to the reaction mixture. The solvent may be a polar aprotic solvent, which may be selected from the group consisting of dimethylformamide, dimethylacetamide (DMA), dimethylsulfoxide (DMSO), sulfolane, or hexamethylphosphoramide (HMPA). The ratio of the solvent to the methyltriethylammonium halide can range from 4 to 5 mL/g, and in certain embodiments is 4.5 mL/g.

The resulting reaction mixture suspension is vigorously stirred. The reaction may be conducted at room temperature, and may be conducted at temperatures between 15° C. and 30° C. and for a time that can range from thirty minutes to three hours, and in certain embodiments is 25° C. for two hours. The reaction produces the methyltriethylammonium tetrahydroborate intermediate and the alkali metal halide.

The methyltriethylammonium tetrahydroborate intermediate is separated from the reaction mixture prior to pyrolysis. The methyltriethylammonium tetrahydroborate intermediate may be removed from the reaction mixture by filtration, wherein the methyltriethylammonium tetrahydroborate intermediate is collected in the filtrate. The methyltriethylammonium tetrahydroborate intermediate is precipitated from the filtrate with a second solvent. The second solvent is preferably different from the first solvent.

The second solvent may be a linear or cyclic ether such as diethyl ether, tetrahydrofuran (THF), 1,4-dioxane, or dimethoxyethane (DME). The ratio of solvent to filtrate may be 2:1 to 3:1 by volume and in certain embodiments is about 2.5:1 by volume. The resulting methyltriethylammonium tetrahydroborate intermediate precipitate is substantially free of the alkali metal halide, which was removed during the filtration step.

The methyltriethylammonium tetrahydroborate intermediate precipitate is recovered by filtration, and may be washed with a solvent that may be a linear or cyclic ether such as diethyl ether, tetrahydrofuran (THF), 1,4-dioxane, or dimethyoxethane (DME), and dried. The total yield of the methyltriethylammonium tetrahydroborate intermediate can reach at least 85% and in certain embodiments reaches 90-97%.

The methyltriethylammonium tetrahydroborate intermediate is subsequently pyrolized. The pyrolysis may be conducted using the same equipment, a reaction vessel outfitted with a distillation device, utilized in the first exemplary embodiment discussed above. The methyltriethylammonium tetrahydroborate intermediate is placed in a reaction vessel, slow-stirred and heated to a temperature of at least 180° C., and in certain embodiments 180° C. to 200° C. The reaction mixture is held at the pyrolysis temperature for a sufficient time for the pyrolysis to take place. In certain embodiments the methyltriethylammonium tetrahydroborate intermediate is held at the pyrolysis temperature for at least one hour, or between one and four hours. The reaction mixture is subsequently allowed to cool to room temperature.

As with the first exemplary embodiment discussed above, the resulting product mixture contains a mixture of methyltriethylammonium decahydrodecaborate and methyltriethylammonium dodecahydrododecaborate. However, the resulting product mixture is substantially free of the alkali metal halide. In certain embodiments the ratio, by weight, of methyltriethylammonium decahydrodecaborate to methyltriethylammonium dodecahydrododecaborate in the product mixture can range between 40:60 and 60:40.

Isolation of Polyhedral Borane Salts

The methyltriethylammonium decahydrodecaborate and methyltriethylammonium dodecahydrododecaborate in the product mixture can be separated based on water solubility.

The product mixture is mixed with cold water. The temperature of the cold water is below 5° C., preferably between 0° C. and 10° C. and in certain embodiments the cold water is ice water at a temperature of about 0° C. The water may be in the form of an aqueous solution, such as a sodium chloride solution. The resulting product mixture solution comprises sufficient water to dissolve the product mixture. The product mixture may comprise between about 25 and 35 (w/w) of the product mixture solution, and in certain embodiments comprises about 30% (w/w) of the product mixture solution. The resulting product mixture solution is stirred to dissolve the product mixture in the product mixture solution, preferably for at least 2 minutes.

The product mixture solution is filtered to produce a filter cake comprising the methyltriethylammonium dodecahydrododecaborate and a product mixture filtrate comprising methyltriethylammonium decahydrodecaborate and a negligible amount of methyltriethylammonium dodecahydrododecaborate. The product mixture filtration step may be repeated one or more times, with the product mixture filtrates being combined. The methyltriethylammonium decahydrodecaborate and methyltriethylammonium dodecahydrododecaborate are further separated as follows:

Separation of Dodecahydrododecaborate

The filter cake is recrystallized from acetonitrile to produce a crystalline residue comprising the methyltriethylammonium dodecahydrododecaborate. In such recrystallization, the filter cake is dissolved in acetonitrile and the methyltriethylammonium dodecahydrododecaborate is recrystallized from the acetonitrile to produce the crystalline residue comprising the methyltriethylammonium dodecahydrododecaborate. The resulting crystalline residue is then washed and dried, in certain embodiments with acetone, to yield the methyltriethylammonium dodecahydrododecaborate polyhedral borane salt comprising the dodecahydrododecaborate dianion. The anion may be a closo-dodecahydrododecaborate anion. The recovery of the closo-dodecahydrododecaborate salt can achieve at least 50-60% recovery of the dodecahydrododecaborate dianion, and in some embodiments can reach 70% recovery.

Separation of Decahydrodecaborate

The decahydrodecaborate dianion is precipitated from the product mixture filtrate as a salt. The decahydrodecaborate dianion may be precipitated from the product mixture filtrate using an ammonium halide. Other compounds that can be used to precipitate the decahydrodecaborate dianion include tetraalkylphosphonium. The ammonium halide may be selected from the group consisting of trialkylammonium halides and tetraalkylammonium halides. In certain embodiments, the ammonium halide is selected from the group consisting of tetrabutylammonium bromide, tetrabutylammonium chloride, tributylammonium chloride, and tributylammonium bromide to produce the corresponding ammonium decahydrodecaborate salts. The halide is added to the product mixture filtrate in an amount sufficient to precipitate the decahydrodecaborate dianion as an ammonium decahydrodecaborate salt. In certain embodiments the halide is added in an amount that is at twice the number of moles of the decahydrodecaborate dianion, and in certain embodiments the molar ratio of halide to decahydrodecaborate dianion is 2.5:1. The decahydrodecaborate salt precipitate is washed with water. The salt may be a closo-decahydrodecaborate salt. The percentage recovery of the decahydrodecaborate anion ($[B_{10}H_{10}]^{2-}$) can reach 40% and in certain embodiments can reach 50-60%.

In certain embodiments, the decahydrodecaborate anion is not precipitated as an ammonium salt, but is isolated and collected from the second filtrate using an ion exchange resin. In one such embodiment, the methyltriethylammonium cation is exchanged for alkali metal cations or ammonium by adding alkali metal or ammonium hydroxide to the ion exchange resin. The decahydrodecaborate is recovered as alkali metal or ammonium salt of the decahydrodecaborate dianion.

Isolation of Amine Boranes

In certain embodiments, amine boranes and amines are recovered from the condensate of the pyrolysis reaction. The pyrolysis reaction is conducted in a reactor attached to a two-stage condensation system. The first stage condenser collects a mixture of methyldiethylamine borane, triethylamine borane, methyldiethylamine, and triethylamine. The second stage condenser collects a mixture of methyldiethylamine and triethylamine. Preferably, non-condensable matter is bubbled through an acid such as hydrochloric acid, sulfuric acid, or acetic acid so that the acid may react with any non-condensed amines, amine borane vapors and/or lower boranes which can form during the reaction in minute amounts and pose a safety concern. The amines and amine boranes may be separated by distillation.

The present invention provides an efficient synthesis and purification of salts of polyhedral boranes, namely decahydrodecaborate and dodecahydrododecaborate, from two inexpensive starting materials—metal alkali tetrahydroborate and tetraalkylammonium halide. Alternative pyrolysis routes are available. Isolation and separation of the products by mostly aqueous treatment of the reaction mixture allows for minimal usage of organic solvents and affords polyhedral borane salts in good yields. Combined yields of the methyltriethylammonium decahydrodecaborate and the methyltriethylammonium dodecahydrododecaborate of over 50% in the reaction product can be achieved. The process for the synthesis of the polyhedral boranes of the present invention uses short reaction times. The process of the present invention also allows for the isolation and characterization of by-products. Amines and amine boranes are valuable side products of the reaction, which can easily be separated and purified.

Synthesis of $^{10}$B-Enriched Polyhedral Boranes

In certain embodiments, the alkali metal tetrahydroborate starting material may be a $^{10}$B-enriched alkali metal tetrahydroborate, such as sodium tetrahydroborate-$^{10}$B and the resulting products may comprise $^{10}$B-enriched decahydrodecaborate and decahydrodecaborate dianions and salts. The $^{10}$B-enriched alkali metal tetrahydroborate may be produced using the process disclosed in co-pending application entitled "Synthesis of Borane Compounds" filed by the same inventors, and given PCT App. No. PCT/US15/14224, which is hereby incorporated herein by reference.

The present invention is further illustrated by the following non-limiting examples:

Example 1

The following example is consistent with the first exemplary embodiment discussed above.

Equipment.

The reactor was a 24" long steel cylinder, 12" in diameter, equipped with thermocouple, pressure gauge, blow-valves, check-valves adjusted at opening pressure 20 psi, and an argon/vacuum switchable valve. The reactor could rotate by means of an electrical motor through a chain gear. The reactor was positioned inside an insulated box containing heating coils and thermocouples connected to the automatic temperature controller. Gases that escaped from the reactor through check-valves were mixed with argon carrier-gas in Teflon lines and then went through a two-stage glass condensation system with the two condensers kept at −15° C. and −78° C., respectively. Non-condensable matter was bubbled through concentrated acetic acid. Approximately 40-50 steel balls (½" in diameter) were used in the reactor as described below.

Synthesis.

Methyltriethylammonium chloride was dried in a reaction vessel under vacuum at 120° C. for 2 hours. The mass of the methyltriethylammonium chloride was calculated based on moisture content (determined by NMR) in such a way that after drying it weighed 3,000 grams. Sodium tetrahydroborate (748 grams) was added to the reaction vessel. Approximately 40-50 steel balls (½" in diameter) were added and the reaction mixture was heated to 120° C. and kept at this temperature for 15 minutes. The reaction mixture was then heated to 150° C. and maintained at that temperature for 1 hour. Finally, the reaction mixture was heated to 185° C. and maintained at that temperature for 7 hours. After that time the reaction mixture was cooled to 170° C. and evacuated to 29" Hg for 2 hours using a 1 L trap at −196° C. The reaction mixture was filled with argon and allowed to cool to room temperature.

Product Isolation.

Isolation of Polyhedral Boranes.

The reaction mixture was determined to contain 17.5% (w/w) of a polyhedral borane mixture where the percentage of (MeNEt$_3$)$_2$[B$_{10}$H$_{10}$] was 54% (w/w) and the percentage of (MeNEt$_3$)$_2$[B$_{12}$H$_{12}$] was 46% (w/w). A 50 gram batch of the dry ground reaction mixture was mixed with 100 milliliters of ice cold water and stirred on a magnetic stirrer for approximately 2 minutes. The precipitate was filtered on a coarse porosity glass frit and then the residue was washed twice with 100 milliliter portions of ice cold water. The filter cake was dissolved in 20 milliliters of acetonitrile and evaporated. The resulting crystalline residue was washed on a glass frit with three separate 3 milliliter portions of acetone and dried by air suction to give 3.00 grams of methyltriethylammonium dodecahydrododecaborate (MeNEt$_3$)$_2$[B$_{12}$H$_{12}$] which corresponded to 75% recovery of [B$_{12}$H$_{12}$]$^{2-}$.

Combined water washings were evaporated, leaving a dry residue. The residue was re-dissolved in 100 milliliters of boiling water and filtered. After cooling, the filtrate was diluted with 200 milliliters of water, and tetrabutylammonium bromide (7.50 g) was added to the filtrate. The white precipitate was filtered, washed with 50 milliliters of water and dried by air suction to give 6.50 grams of tetrabutylammonium decahydrodecaborate (TBA$_2$ [B$_{10}$H$_{10}$]), which corresponded to 80% recovery of [B$_{10}$H$_{10}$]$^{2-}$.

Isolation of Amine Boranes.

The reaction condensate was a mixture of four compounds: methyldiethylamine, triethylamine, methyldiethylamine borane, and triethylamine borane. Amines and amine boranes were separated by distillation. 1,640 grams of the reaction condensate was placed into a 3 liter 2-necked round-bottom flask equipped with a thermometer, stirring bar, and distillation head. The distillation head was connected to a 1 liter receiving flask and a mineral oil bubbler. Distillation was performed by stirring on a heating mantle until the temperature in the distillation flask reached 170° C. NMR analysis of the distillate (590 g) showed a mixture of MeNEt$_2$ (30% w/w) and Et$_3$N (70% w/w). The distillation flask contained 1,040 grams of an amine borane mixture with MeNEt$_2$.BH$_3$ (46% w/w) and Et$_3$N.BH$_3$ (54% w/w).

Examples 2 and 3

Equipment for Examples 2 and 3.

A one-gallon steel pressure reactor manufactured by Parr Instruments was used for the synthesis of polyhedral boranes. The reactor was attached to a two-stage condensation system. Vapors from the reactor entered the first stage condensation system via a 0.5-inch Teflon tubing. The first stage of the condensation system was a vertical steel condenser equipped with a steel reservoir. The condenser was kept at −15° C. by means of a recirculating chiller. The first stage condensation system was connected to the second stage via a steel manifold. The manifold was constructed in a way that the reactor and the first stage condensation system could be separated from the rest of the system, evacuated, and filled with an inert gas. The second stage of the condensation system was a glass Dewar condenser with an attached 500 milliliter single-necked round-bottom receiving flask. The condenser was kept at −78° C. by a 2-propanol/dry ice mixture. Exhaust from the second stage condenser was mixed with a carrier gas (argon) and bubbled through glacial acetic acid. The reactor was equipped with a temperature controller. The controller thermocouple was positioned between the heater and the outer wall of the reactor. The second thermocouple was positioned in a thermocouple well in the reactor lid and was used to measure the temperature of the reaction mixture.

Example 2

The following example is consistent with the first exemplary embodiment discussed above.

Synthesis.

Methyltriethylammonium chloride was dried in a vacuum oven prior to reaction at 140° C. during 3 hours. The weight of the methyltriethylammonium chloride was calculated based on moisture content (determined by NMR) in such way that after drying it weighed 200 grams (1.32 mol). Sodium tetrahydroborate (50 grams, 1.32 mol) was mixed with methyltriethylammonium chloride in the reactor. The reactor was sealed, evacuated, and filled with argon. Upon slow stirring, the reaction mixture was heated to 185° C. (as measured by the internal thermocouple) for one hour. After that time the heater was switched off and the reactor was allowed to cool to room temperature. Analysis of the solid reaction products by NMR showed that it contained methyltriethylammonium decahydrodecaborate and dodecahydrododecaborate wherein the ratio of the two products to one another ranged from 40:60 to 60:40 by weight, respectively. The total concentration of the combined polyhedral boranes in the reaction mixture was measured as ranging from 15% to 25% by weight of the total reaction mixture. The rest of the reaction mixture was sodium chloride. The first stage condensate contained a mixture of methyldiethylamine borane and triethylamine borane wherein the average molar ratio of methyldiethylamine borane to triethylamine borane was 1:1. The second stage condensation system contained a mixture of methyldiethylamine and triethylamine.

Product Isolation,

Isolation of Polyhedral Boranes from Mixture Containing Sodium Chloride.

The reaction mixture was determined to contain 15-25% (w/w) of a polyhedral borane mixture wherein the ratio of methyltriethylammonium decahydrodecaborate to dodecahydrododecaborate ranged from 40:60 to 60:40 by weight. A 50 gram batch of the ground reaction mixture was mixed with 100 milliliters of ice cold water and stirred on a magnetic stirrer for approximately 2 minutes. The precipitate was filtered on a coarse porosity glass frit, and the residue was subsequently washed twice with 100 milliliter portions of ice-cold water. Combined water washings were evaporated to leave a dry residue. The residue was re-dissolved in 100 milliliters of boiling water and filtered. After cooling, the filtrate was diluted with 200 milliliters of water and tetrabutylammonium bromide was added to the filtrate. The white precipitate was filtered, washed with 50 milliliters of water, and dried by air suction to give 5.5-6.5 grams of tetrabutylammonium decahydrodecaborate (TBA)$_2$[B$_{10}$H$_{10}$], which corresponded to 75-80% recovery of [B$_{10}$H$_{10}$]$^{2-}$. The filter cake was dissolved in 20 mL of acetonitrile and evaporated. The crystalline residue was washed on a glass frit with three separate 3 milliliter portions of acetone and dried by air suction to give 2.5-3.0 g of methyltriethylammonium dodecahydrododecaborate (MeNEt$_3$)$_2$[B$_{12}$H$_{12}$], which corresponded to 65-75% recovery of [B$_{12}$H$_{12}$]$^{2-}$.

Example 3

The following example is consistent with the second exemplary embodiment discussed above.

Synthesis.

Anhydrous methyltriethylammonium chloride (245.7 grams, 1.62 mol) and sodium borohydride (60 grams, 1.62 mol) were mixed as solids in a 2-liter flask and 900 milliliters of dimethylformamide was added to the mixture. The suspension was vigorously stirred at room temperature for 2 hours and subsequently filtered. Diethyl ether (2.5 liters) was added to the filtrate and the formed precipitate was filtered, washed with 500 milliliters of diethyl ether and dried in vacuum of an oil pump. The total yield of methyltriethylammonium tetrahydroborate was 190-205 g (90-97%). The compound was extremely hygroscopic.

Methyltriethylammonium tetrahydroborate (500 grams, 3.84 mol) was placed into the reactor, and the reactor was sealed, evacuated, and filled with argon. Upon slow stirring, the reaction mixture was heated to 185° C. (as measured by the internal thermocouple) for 1 hour. After that time the heater was switched off and the reactor was allowed to cool to room temperature. Analysis of the solid reaction products (140-200 grams) by NMR showed that the ratio by weight of the methyltriethylammonium decahydrodecaborate to methyltriethylammonium dodecahydrododecaborate ranged from 40:60 to 60:40. The first stage condensate contained a mixture of methyldiethylamine borane and triethylamine borane wherein the average molar ratio of methyldiethylamine borane to triethylamine borane was 1:1. The second stage condensation system contained a mixture of methyldiethylamine and triethylamine.

Product Isolation.

Isolation of Polyhedral Boranes from Sodium Chloride-Free Mixture.

A 100 gram batch of the ground reaction mixture was mixed with 300 milliliters of ice cold water and stirred on a magnetic stirrer for 4-5 minutes. The precipitate was filtered on a coarse porosity glass fit and then the procedure was repeated twice (the total volume of water per 100 gram batch was 900 milliliters). The decahydrodecaborate anion was precipitated by the addition of tributylammonium chloride, filtered, washed with water and diethyl ether and dried in vacuum of an oil pump. The weight of the isolated tributylammonium decahydrodecaborate $(Bu_3NH)_2[B_{10}H_{10}]$ varied from batch to batch from 30-40 grams which corresponded to 50-60% recovery of $[B_{10}H_{10}]^{2-}$ dianion. The residue was crystallized from acetonitrile to give 25-30 grams of methyltriethylammonium dodecahydrododecaborate $(MeNEt_3)_2[B_{12}H_{12}]$ which corresponded to 50-60% recovery of $[B_{12}H_{12}]^{2-}$ dianion.

We claim:

1. A method for synthesizing mixtures of salts of polyhedral boranes, comprising:
    combining a methyltriethylammonium halide with an alkali metal tetrahydroborate in a reaction mixture;
    reacting the methyltriethylammonium halide and the alkali metal tetrahydroborate to form a methyltriethylammonium tetrahydroborate intermediate and an alkali metal halide; and
    pyrolyzing the methyltriethylammonium tetrahydroborate intermediate to produce a product mixture comprising methyltriethylammonium decahydrodecaborate and methyltriethylammonium dodecahydrododecaborate.

2. The method of claim 1, wherein the reacting step and the pyrolyzing step are performed as a continuous heating step; and wherein the pyrolyzing step comprises pyrolyzing the methyltriethylammonium tetrahydroborate intermediate in situ in the reaction mixture.

3. The method of claim 1, further comprising:
    prior to the reacting step, adding to the reaction mixture a polar aprotic solvent; and
    prior to the pyrolyzing step, separating the methyltriethylammonium tetrahydroborate intermediate from the reaction mixture.

4. The method of claim 3, wherein the polar aprotic solvent is selected from the group consisting of dimethylformamide, dimethylacetamide, dimethylsulfoxide, sulfolane, and hexamethylphosphoramide.

5. The method of claim 3, wherein the intermediate separating step comprises:
    filtering the reaction mixture to produce a filtrate comprising the methyltriethylammonium tetrahydroborate intermediate; and
    precipitating the methyltriethylammonium tetrahydroborate intermediate from the filtrate with a second solvent.

6. The method of claim 1, wherein the pyrolyzing step is conducted at a temperature between 180° C. and 200° C. for between 1 and 4 hours.

7. The method of claim 1, wherein the methyltriethylammonium halide is selected from the group consisting of methyltriethylammonium chloride and methyltriethylammonium bromide.

8. The method of claim 1, wherein the alkali metal tetrahydroborate is selected from the group consisting of sodium tetrahydroborate and potassium tetrahydroborate.

9. The method of claim 5, wherein the second solvent is a linear or cyclic ether.

10. The method of claim 9, wherein the linear or cyclic ether is selected from the group consisting of diethyl ether, tetrahydrofuran, 1,4-dioxane, and dimethoxyethane.

11. The method of claim 1, further comprising separating the methyltriethylammonium decahydrodecaborate and the methyltriethylammonium dodecahydrododecaborate in the product mixture based on water solubility.

12. The method of claim 11, wherein said product mixture contains the alkali metal halide and said product mixture separating step comprises:
    combining the product mixture with cold water to produce a product mixture solution;
    filtering the product mixture solution to produce a filter cake comprising methyltriethylammonium dodecahydrododecaborate and a product mixture filtrate comprising methyltriethylammonium decahydrodecaborate, methyltriethylammonium dodecahydrododecaborate and the alkali metal halide.

13. The method of claim 12, further comprising the step of purifying the methyltriethylammonium dodecahydrododecaborate from the filter cake.

14. The method of claim 13, wherein the purifying step comprises dissolving the filter cake in acetonitrile and recrystallizing the methyltriethylammonium dodecahydrododecaborate from the acetonitrile to produce a crystalline residue comprising the methyltriethylammonium dodecahydrododecaborate.

15. The method of claim 12, further comprising removing methyltriethylammonium dodecahydrododecaborate from the product mixture filtrate.

16. The method of claim 15, wherein the removing step comprises
    evaporating the water in the product mixture filtrate to form a residue comprising the methyltriethylammonium decahydrodecaborate;
    re-dissolving the residue in additional water to produce a methyltriethylammonium decahydrodecaborate solution;
    filtering the methyltriethylammonium decahydrodecaborate solution to form a second filtrate comprising the methyltriethylammonium decahydrodecaborate, wherein decahydrodecaborate is present as a dianion; and
    precipitating the decahydrodecaborate dianion from the second filtrate.

17. The method of claim 16, wherein the precipitating step comprises adding to the second filtrate a halide selected from the group consisting of trialkylammonium halides, tetraalkylammonium halides and tetraalkylphosphonium halides.

18. The method of claim 17, wherein the halide is an ammonium halide selected from the group consisting of tetrabutylammonium bromide, tetrabutylammonium chloride, tributylammonium chloride, and tributylammonium bromide.

19. The method of claim 15, wherein the removing step comprises evaporating the water in the product mixture filtrate to form a residue comprising the methyltriethylammonium decahydrodecaborate;

re-dissolving the residue in additional water to produce a methyltriethylammonium decahydrodecaborate solution;

filtering the methyltriethylammonium decahydrodecaborate solution to form a second filtrate comprising the methyltriethylammonium decahydrodecaborate wherein decahydrodecaborate is present as a dianion; and isolating the decahydrodecaborate dianion using an ion exchange resin.

20. The method of claim 3, wherein said methyltriethylammonium decahydrodecaborate and said methyltriethylammonium dodecahydrododecaborate in said product mixture are separated based on water solubility, and wherein said product mixture separating step comprises:

combining the product mixture with cold water to produce a product mixture solution;

filtering the product mixture solution to produce a filter cake comprising methyltriethylammonium dodecahydrododecaborate and a product mixture filtrate comprising methyltriethylammonium decahydrodecaborate wherein decahydrodecaborate is present as a dianion.

21. The method of claim 20, further comprising the step of purifying the methyltriethylammonium dodecahydrododecaborate from the filter cake.

22. The method of claim 21, wherein the purifying step comprises dissolving the filter cake in acetonitrile and recrystallizing the methyltriethylammonium dodecahydrododecaborate from the acetonitrile to produce a crystalline residue comprising the methyltriethylammonium dodecahydrododecaborate.

23. The method of claim 20, wherein the product mixture separating step further comprises precipitating the decahydrodecaborate dianion from the product mixture filtrate.

24. The method of claim 23, wherein the decahydrodecaborate dianion precipitating step comprises adding to the product mixture filtrate a halide selected from the group consisting of trialkylammounium halides, tetraalkylammonium halides and tetraalkylphosphonium halides.

25. The method of claim 24, wherein the halide is an ammonium halide selected from the group consisting of tetrabutylammonium bromide, tetrabutylammonium chloride, tributylammonium chloride, and tributylammonium bromide.

26. The method of claim 20, wherein the product mixture separating step further comprises isolating the decahydrodecaborate dianion using an ion exchange resin.

27. The method of claim 1, wherein the pyrolizing step is conducted in a reactor attached to a two-stage condensation system, wherein a first stage condenser collects a mixture of methyldiethylamine borane, triethylamine borane, methyldiethylamine, and triethylamine, and a second stage condenser collects a mixture of methyldiethylamine and triethylamine.

28. The method of claim 27, wherein said mixture of methyldiethylamine borane, triethylamine borane, methyldiethylamine, and triethylamine is collected and distilled by fractional distillation to separate the methyl di ethyl amine borane, triethylamine borane, methyldiethylamine, and triethylamine.

29. The method of claim 27, wherein the mixture of methyldiethylamine and triethylamine is collected and distilled by fractional distillation to separate the methyldiethylamine and triethylamine.

30. The method of claim 1, wherein the alkali metal tetrahydroborate is $^{10}$B-enriched alkali metal tetrahydroborate.

31. The method of claim 30, wherein the $^{10}$B-enriched alkali metal tetrahydroborate is synthesized by:

first, reacting $^{10}$B-enriched boric acid with a $C_2$-$C_4$ alcohol in a reaction mixture that does not include toluene, xylene, mesitylene, benzene, or 1,2-dichlorhoethane to produce trialkylborate-$^{10}$B;

second, reacting the trialkylborate-$^{10}$B with a metal aluminum hydride in the presence of an amine to produce amine borane-$^{10}$B; and third, reacting the amine borane-$^{10}$B with a reagent selected from the group consisting of alkali metal hydride and alkali metal methoxide to produce alkali metal tetrahydroborate-$^{10}$B.

32. A method for synthesizing mixtures of salts of polyhedral boranes, comprising:

combining a methyltriethylammonium halide with an alkali metal tetrahydroborate in a reaction mixture; and pyrolizing the reaction mixture to produce a product mixture comprising methyltriethylammonium decahydrodecaborate, methyltriethylammonium dodecahydrododecaborate and an alkali metal halide.

33. A method for synthesizing mixtures of salts of polyhedral boranes, comprising:

combining a methyltriethylammonium halide, an alkali metal tetrahydroborate and a solvent selected from the group consisting of dimethylformamide, dimethylacetamide, dimethylsulfoxide, and sulfolane, hexamethylphosphoramide to form a methyltriethylammonium tetrahydroborate intermediate and an alkali metal halide;

separating the methyltriethylammonium tetrahydroborate intermediate from the reaction mixture; and pyrolizing the methyltriethylammonium tetrahydroborate intermediate to produce a product mixture comprising methyltriethylammonium decahydrodecaborate and methyltriethylammonium dodecahydrododecaborate.

34. A method for separating a methyltriethylammonium decahydrodecaborate and a methyltriethylammonium dodecahydrododecaborate from a mixture based on water solubility wherein the separating step comprises:

combining the mixture with cold water to produce a mixture solution; and filtering the mixture solution to produce a filter cake comprising methyltriethylammonium dodecahydrododecaborate and a product mixture filtrate comprising methyltriethylammonium decahydrodecaborate.

\* \* \* \* \*